United States Patent
Kakulapati et al.

(10) Patent No.: US 6,239,313 B1
(45) Date of Patent: May 29, 2001

(54) PROCESS FOR THE SOLID STATE SYNTHESIS OF ENANTIOPURE β-AMINOALCOHOLS FROM RACEMIC EPOXIDES

(75) Inventors: Rama Rao Kakulapati; Bhanumathi Nanduri; Rajender Reddy Eleti, all of Hyderabad, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,384

(22) Filed: Mar. 24, 2000

(51) Int. Cl.⁷ .................................................. C07C 213/00
(52) U.S. Cl. ........................................... 564/349; 564/351
(58) Field of Search ...................................... 564/349, 351

(56) References Cited

U.S. PATENT DOCUMENTS 4,018,824 * 4/1977 Tsukamoto et al. .................. 564/348
5,064,863 * 11/1991 Alig et al. ............................. 514/653

* cited by examiner

*Primary Examiner*—Samuel Barts
(74) *Attorney, Agent, or Firm*—Darby & Darby

(57) ABSTRACT

The invention relates to a process for the solid state synthesis of enantiopure β-aminoalcohols by preparing inclusion complexes of aryloxyepoxide with cyclodextrin by adding an epoxide in equimolar ratio in an organic solvent to an aqueous solution of cyclodextrin, reacting the cyclodextrin complex of aryloxyepoxide with a nucleophile in solid state by intimately grinding the mixture using a mortar and pestle, continuing the mixing till the starting epoxide disappeared on tlc, removing excess amines under vacuum, extracting the β-aminoalcohols produced with a solvent with yields of more than 50% and enantioselectivity of upto 100%.

9 Claims, No Drawings

PROCESS FOR THE SOLID STATE SYNTHESIS OF ENANTIOPURE B-AMINOALCOHOLS FROM RACEMIC EPOXIDES

FIELD OF THE INVENTION

The present invention relates to a process for the solid state synthesis of enantiopure β-aminoalcohols from racemic epoxides. More particularly, the present invention relates to a process for the solid state synthesis of enantiopure β-aminoalcohols from racemic epoxides by the dynamic kinetic resolution involving enantiodifferentiating racemisation in crystalline cyclodextrin complexes.

The novel phenomenon of converting racemic substrates to enantiopure products is illustrated by the synthesis of enantiopure β-aminoalcohols by dynamic kinetic resolution involving chiral cyclodextrins by supramolecular catalysis under solid state conditions.

BACKGROUND OF THE INVENTION

Dynamic kinetic resolution involves the conversion of racemic substrate into a single stereoisomer of the product by inter-conversion of the reactant isomers by racemisation, making removal of one of the isomers as the rate determining step. Dynamic kinetic resolution also overcomes the limitation of conventional kinetic resolution where the maximum yield of one stereoisomer of the starting material or product is only 50%. Dynamic kinetic resolution, though of great significance in asymmetric synthesis to get a single enantiomer of the product from racemic substrate, is not a widespread phenomenon. Only a few cases have been reported so far (R. S. Ward, *Tetrahedron Asymmetry*, 1996, 1475). However, in these cases the substrates involved are made chirally labile either chemically, biochemically or thermally. There is also a stray reference by F. Toda and K. Tanaka in *Chem. Lett.*, 1983, 661, of converting racemic cyanohydrin into a single enantiomer by complexation with brucine. However, there has been no attempt so far to involve chirally stable racemic epoxides by any means in dynamic kinetic resolution by reaction with amines for obtaining enantiopure β-aminoalcohols that have a high potential as intermediates for the synthesis of wide range of biologically active compounds and as precursors in asymmetric transformations. Until now dynamic kinetic resolution has not been carried out by supramolecular catalysis involving cyclodextrins.

Accordingly, studies were undertaken to see the possibility of involving chirally stable, easily accessible and inexpensive racemic epoxides for the synthesis of enantiopure β-aminoalcohols by dynamic kinetic resolution through supramolecular catalysis in cyclodextrins.

OBJECTS OF THE INVENTION

The main object of the invention is to provide a process for the synthesis of enantiopure β-aminoalcohols from racemic epoxides by creating conditions for enantiodifferentiating racemisation in cyclodextrin complexes.

It is another object of the invention to provide a process for the formation of enantiomerically pure products from racemic epoxides by dynamic kinetic resolution through supramolecular catalysis involving cyclodextrins by enantiodifferentiating racemisation since cyclodextrins are chiral and mimic enzymes.

It is another object of the invention to provide a process for the solid state synthesis of enantiopure β-aminoalcohols that overcomes the limitations of kinetic resolution.

SUMMARY OF THE INVENTION

The structures of α-cyclodextrin, β-cyclodextrin and γ-cylodextrin are indicated below in Table I and represented by reference numerals 1, 2 and 3 respectively.

TABLE 1

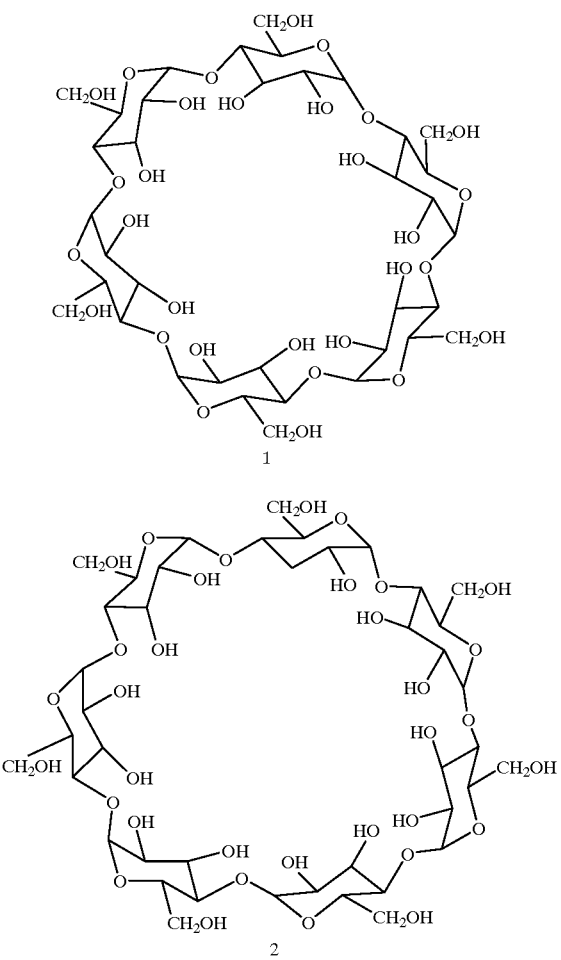

TABLE 1-continued

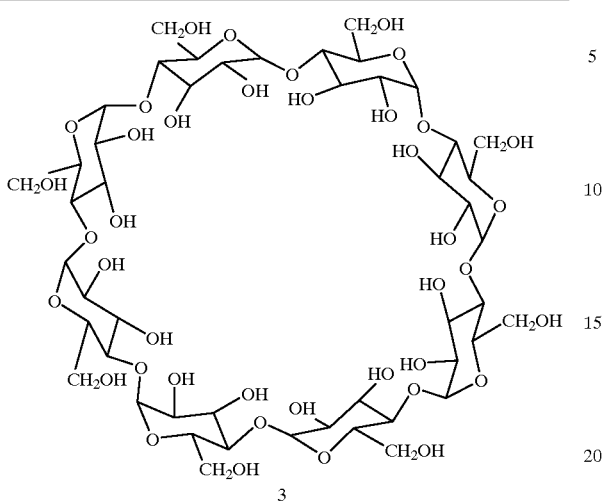

The following Table II discloses the reaction of cyclodextrin complex of racemic epoxides 1 with amines 2 and 3 to form enantiopure β-aminoalcohols 4 (4a, 4b, 4c and 4d) and 5(5a, 5b, 5c and 5d) respectively:

TABLE 2

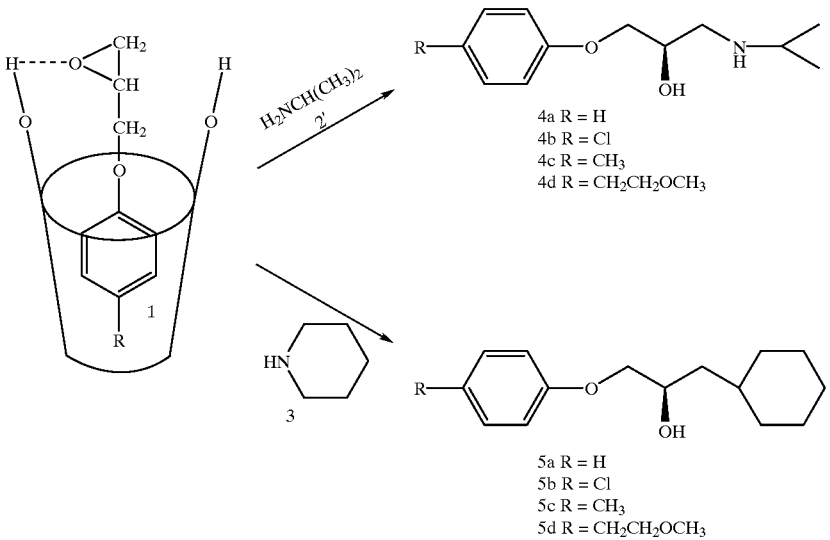

The racemisation of aryloxyepoxides is shown in Table III below:

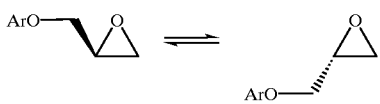

The present invention discloses a process for the solid state synthesis of enantiopure β-aminoalcohols from racemic epoxides by dynamic kinetic resolution involving enantiodifferentiating racemisation in crystalline cyclodextrin complexes, which comprises synthesis of various racemic aryloxyepoxides to obtain their inclusion complex with cyclodextrins, reacting the epoxide of the cyclodextrin complex with amines under solid state conditions, extracting the product with solvent, removing the solvent and amine in vacuo and purifying the product β-aminoalcohol by the formation of hydrochloride.

Accordingly the invention relates to a process for the solid state synthesis of enantiopure β-aminoalcohols of formula VI form racemic epoxides which comprises:

(a). preparing inclusion complexes of aryloxyepoxide with cyclodextrin by adding an epoxide in equimolar ratio in an organic solvent to an aqueous solution of cyclodextrin at a temperature ranging between 30–80° C.;

(b). reacting the cyclodextrin complex of aryloxyepoxide with a nucleophile in solid state by intimately grinding the mixture using a mortar and pestle;

(c). continuing the mixing till the starting epoxide disappeared on tlc within a period ranging between 3–12 hours;

(d). removing excess amines under vacuum;

(e). extracting the β-aminoalcohols of formula 4 or 5 with a solvent with yields of more than 50% and enantioselectivity of upto 100%.

In one embodiment of the invention the substrates forming the inclusion complexes with cyclodextrins are selected from aryloxy epoxides that are optionally substituted with halo, alkyl or substituted alkyl.

In another embodiment of the invention the cyclodextrins that form an inclusion complex with aryloxyepoxides are cyclic oligosaccharides comprising six glucose units (α-cyclodextrin), seven glucose units (β-cyclodextrin) or eight glucose units (γ-cyclodextrin).

In a yet another embodiment of the invention the epoxide cyclodextrin complexes may be prepared by adding the epoxide in equimolar ratio in solvents such as methanol, ethanol, acetone, etc. to an aqueous solution of cyclodextrin.

In a further embodiment of the invention, the reaction of cyclodextrin complex of the aryloxyepoxide with amines may be carried out in solid state by intimately grinding the mixture using mortar and pestle or in liquid state using water as a reaction medium.

In another embodiment of the invention, the solvents used for preparing inclusion complexes are selected from the group comprising of methanol, ethanol, and acetone.

In a further embodiment of the invention, the solvent used for extracting the aminoalcohols are selected from the group comprising of dichloromethane, chloroform, ethyl acetate and methanol.

In another embodiment of the invention, the nucleophiles used are amines.

As a result of intensive study with the aim of achieving the above-mentioned objectives, a new process for the synthesis of enantiopure β-aminoalcohols from racemic epoxides by dynamic kinetic resolution involving enantiodifferentiating racemisation in crystalline cyclodextrin complexes has been achieved for the first time under solid state conditions.

DETAILED DESCRIPTION OF THE INVENTION

Accordingly, the present investigation deals with a process for the solid state synthesis of enantiopure β-aminoalcohols of formula VI (as shown in Table IV below) from racemic epoxides by dynamic kinetic resolution by dynamic kinetic resolution through supramolecular catalysis in cyclodextrin complexes.

1. A phenyl ring that can best fit into the cyclodextrin cavity to form an inclusion complex;
2. A functional group at the stereogenic center to form strong interaction with the secondary hydroxyl groups at the cyclodextrin cavity entrance.

Aryloxyepoxides have been chosen as substrates for the formation of inclusion complexes with cyclodextrins. The inclusion complexes of arylepoxides with cyclodextrins are prepared by adding the epoxides in equimolar ratio in solvents such as methanol, ethanol, acetone and the like at temperatures varying between 30 to 80° C. The formation of inclusion complex of epoxide with cyclodextrin was determined by $^1H$-nmr spectroscopy. The reaction of the cyclodextrin complex of aryloxyepoxide with nucleophiles such as amines was carried out in solid state by intimately grinding the mixture using mortar and pestle, since this reaction in liquid state using water as the reaction medium yielded only racemic β-aminoalcohols of the general formulae 4 and 5 as shown in Table II above. The reactions in solid state created conditions for racemisation and also led to better chiral recognition where the movement of the guest molecule is restricted. The reaction in solid state is carried out as shown in the reaction scheme (Table II) above. An intimate mixture of the epoxide-1-cyclodextrin complex of the formula 1 with the amine of the formula 2' or 3' was mixed in an agate mortar using a pestle and the mixing continued until the starting epoxide disappeared on tlc (3–12hrs.). The time taken was always dependent on frequency of mixing. However, the amine of formula 2' was

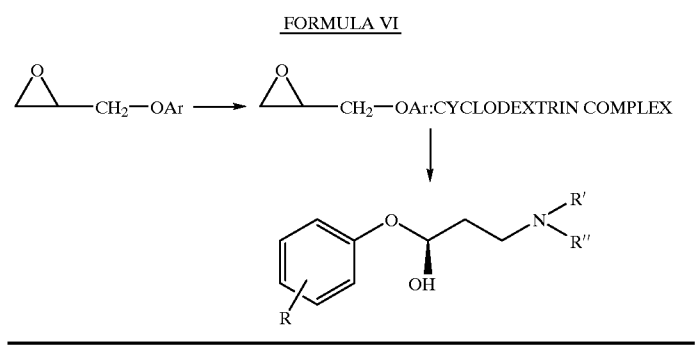

FORMULA VI

The synthesis of each compound is described hereinbelow in detail.

The first step in the process comprises formation of an inclusion complex of aryloxyepoxides of the general formula 1 with cyclodextrins as shown above in Table II.

The cyclodextrins of the general formulae 1, 2 and 3 shown above in Table I are cyclic oligosaccharides possessing hydrophobic cavities and mimic enzymes in their capability to bind substrates selectively and catalyse chemical reactions. They catalyse reactions by supramolecular catalysis involving reversible formation of Host: Guest complexes with substrates by non-covalent bonding as seen in enzymes. Since the cyclodextrin cavity is chiral in nature, it can induce asymmetric reactions. It can discriminate and form complexes with different enantiomers of racemates. The following criteria have to be fulfilled to ensure rigidity for chiral recognition by cyclodextrins:

taken in excess due to its volatility and was added intermittently during the course of mixing. The excess amine was removed under vacuum and the aminoalcohol of formula 4 or 5 was extracted with solvents such as dichloromethane, chloroform, ethylacetate, methanol and the like. The yields obtained were more than 50% and the enantioselectivity observed was excellent with an ee of upto 100% in compounds 4b and 5b. The β-aminoalcohols obtained using β-cyclodextrin—aryloxyepoxide of formula 1 show higher enantioselectivity compared with α-cyclodextrin or γ-cyclodextrin-aryloxyepoxide (1) complex. Hence the reactions with the various amines 2' and 3' were carried out using β-cyclodextrin-aryloxyepoxide (1) complex. These aminoalcohols of formula 4 and 5 have been shown to have R configuration by comparison of the sign of optical rotation with those of known compounds as described in H. Takahashi, S. Sakuraba, H. Takeda and K. Achiwa *J. Am. Chem. Soc.* 1990, 112, 5876.

The mechanism for the formation of enantiopure β-aminoalcohols of the formula 4 and 5 from the racemic epoxides (1) may be postulated as follows:

The fact that the epoxide (1) isolated from the cyclodextrin complex is racemic and the yields of the aminoalcohols 4 and 5 were more than 50%, kinetic resolution is not operating under these conditions as then only a maximum of 50% conversion can be expected. Hence, in the present invention, interconversion of one of the enantiomers of the epoxide 1 is required to get single enantiomer of the product as indicated below:

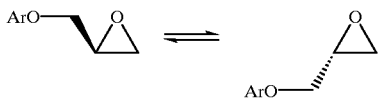

This is possible through a process called racemisation that is controlled entirely by entropy effects as described in: 1. *"Stereodifferentiating reactions, the nature of asymmetric reactions"* by Y. Izumi and A. Tai, Academic Press, New York, 1977, 169–177; 2. *"Stereochemistry of Organic Compounds"*, by E. L. Eliel and S. H. Wilen, John Wiley and Sons, Inc. , New York, 1994, 424–427. This can take place in the present case by the ring opening of the epoxide facilitated by the energy generated in the grinding process under the solid state conditions.

When one of the enantiomeric forms of the epoxide 1 in β-cyclodextrin cavity due to its favourable geometry is captured selectively by the external amine 2 or 3, it leads to the formation of an enantiomerically pure aminoalcohol 4 or 5 starting from the racemic epoxide. Thus dynamic kinetic resolution is operating involving cyclodextrin under the reaction conditions leading to enantiomerically pure aminoalcohols (4 and 5). It has been shown for the first time that enantiopure β-aminoalcohols (4 and 5) of high potential can be formed from the easily accessible and inexpensive racemic epoxides 1 by dynamic kinetic resolution involving enantiodifferentiating racemisation through supramolecular catalysis in cyclodextrin complexes under solid state conditions.

The process of the invention will now be described with reference to the following examples that are by way of illustration only and should not be considered as limiting the scope of the invention in any manner.

The substrate—cyclodextin complexes were made as described earlier (1. *J. Chem. Soc. Chem. Commun.,* 1989, 342; 2. *Synth. Commun.,* 1993, 23, 1877). Enantiomeric excesses (ee) of the products β-aninoalcohols 4 and 5 were determined by chiral HPLC analysis. The conditions employed for chiral HPLC analysis were as follows. The analyses were carried out on HPLC Instrument Hewlett Packard HP 1090 with the chiral column "Diacel chiralcel OD (0.46 cm φ×25 cm) using hexane: 2-propanol: diethylamine (80:20:0.1) as eluent at a flow rate of 0.5 ml/minute, using UV detection (254 nm).

EXAMPLE 1

1-(Isopropylamino)-3-phenoxy-2-propanol (4a):

The β-cyclodextrin complex of the epoxide 3- phenoxy-1,2-epoxypropane (12.85 g) was taken in agate mortar and the isopropylamine 2 (0.59 g=0.86 ml) was added while mixing intimately. After continuously grinding for 30 minutes, excess amine 2 at the rate of 0.86 ml every 30 minutes was added until the starting epoxide 1 disappeared on tlc (3 hours). (tlc:2% methanol:dichloromethane). The product was extracted with ethylacetate, the solvent and the excess amine were removed in vacuo. The product may be purified by formation of hydrochloride by dissolving in 2N hydrochloric acid, washing with diethyl ether and regenerating with 10% sodium bicarbonate solution. The product was then extracted with ethyl acetate, dried over anhydrous sodium sulphate, filtered and the solvent removed in vacuo.

Yield (isolated): 1.65 gms. m.p.: 85–87° C.

$[\alpha]D^{25}$=+10.8 (1.0 MeOH) ee: 73.8% (chiral HPLC)

EXAMPLE 2

1-(Isopropylamino)-3-(4-chlorophenoxy)-2-propanol (4b):

The epoxide 3-(4-chlorophenoxy)-1,2-epoxypropane β-cyclodextrin complex (13.20 g) was ground intimately with excess isopropylamine 2 (2.95 g=4.3 ml added at the rate of 0.86 ml every 30 minutes) in agate mortar until the starting epoxide disappeared on tlc after 3 hours. The product was extracted with ethylacetate, the solvent and the excess amine were removed in vacuo. The product may be purified by dissolving in 2N hydrochloric acid and regenerating with 10% sodium bicarbonate solution.

Yield (isolated): 1.83 gms. m.p.: 247–249° C.

$[\alpha]D^{25}$=+14.8 (c 1.0 MeOH) ee: 100% (chiral HPLC)

EXAMPLE 3

1-(Isopropylamino)-3-(4-methylphenoxy)-2-propanol (4c):

The β-cyclodextrin -epoxide, 3-(4-methylphenoxy)-1,2-epoxypropane complex (12.99 g) was ground with isopropylamine 2 (0.59 g=0.86 ml) in agate mortar for 30 minutes and then excess isopropylamine was added at the rate of 0.86 ml every 30 minutes until the starting epoxide disappeared on tlc after 3 hours. The product was extracted with ethylacetate and the solvent evaporated. It may be purified by formation of hydrochloride in 2N hydrochloric acid and regeneration with 10% sodium bicarbonate solution.

Yield (isolated): 1.60 gms. m.p.: 77–78° C.

$[\alpha]D^{25}$=+13.2 (c 1.0 MeOH) ee: 89% (chiral HPLC)

EXAMPLE 4

1-(Isopropylamino)-3-[4[(2- methoxyethyl)phenoxy]-2-propanol (4d):

The epoxide 3-[4[(2- methoxyethyl)phenoxy] 1,2-epoxypropane β-cyclodextrin complex (13.43 g) was ground in agate mortar with excess isopropylamine (2.95 g=4.3 ml added at the rate of 0.86 ml every 30 minutes until the starting epoxide completely reacted as seen by tlc (3 hours)]. The product was extracted with ethylacetate, the solvent and the excess amine were removed in vacuo. The product nay be purified by the formation of hydrochloride.

Yield (isolated): 1.87 gms. Viscous liquid $[\alpha]D^{25}$=+12.6 (c 1.0 MeOH) ee: 85% (chiral HPLC)

EXAMPLE 5

1-(1-piperidinyl)-3-phenoxy-2-propanol (5a):

The epoxide 3-phenoxy-1,2-epoxypropane-β-cyclodextrin complex (12.85 g) and piperidine (0.85 g=0.99 ml) were ground intimately in agate mortar until the starting epoxide disappeared completely on tlc (3 hours). The product was extracted with ethylacetate and the solvent was removed in vacuo. The product may be purified by the formation of hydrochloride.

Yield (isolated): 1.74 gms. m.p.; 50–51° C.

$[\alpha]D^{25}$=+0.4 (c 1.0 MeOH) ee: 1.4% (chiral HPLC)

EXAMPLE 6

1-(1-piperidinyl)-3-(4-chlorophenoxy)-2-propanol (5b):

The β-cyclodextrin-epoxide, 3-(4-chlorophenoxy)-1,2-epoxypropane complex (13.20 g) was ground intimately with piperidine (0.85 g=0.99 ml) in agate mortar until the starting epoxide disappeared on tlc (3 hours). The product was extracted with ethylacetate and the solvent was removed in vacuo. The product may be purified by formation of hydrochloride in 2N hydrochloric acid and regenerating with 10% sodium bicarbonate solution.

Yield (isolated): 1.88 gms m.p.: 73–74° C.

$[\alpha]D^{25}$=+13.8 (c 1.0 MeOH) ee; 100%(chiral HPLC)

EXAMPLE 7

1-(1-piperidinyl)-3-(4-methylphenoxy)-2-propanol (5c):

The β-cyclodextrin-epoxide, 3-(4- methylphenoxy)-1,2-epoxypropane complex (12.99 g) and piperidine (0.85 g=0.99 ml) were ground intimately in agate mortar until the starting epoxide completely reacted as seen by tlc (3 hours). The product was then extracted with ethylacetate and the solvent was removed in vacuo. The product may be purified by formation of hydrochloride.

Yield (isolated): 1.89 gms. m.p.: 49–50° C.

$[\alpha]D^{25}$=+0.4 (c 1.0 MeOH) ee: 0.8% (chiral HPLC)

EXAMPLE 8

1-(1-piperidinyl)-3-[4-(methoxyethyl)phenoxy]-2-propanol (5d):

The epoxide 3-[4[(2-methoxyethyl)phenoxy] 1,2-epoxypropane β-cyclodextrin complex (13.43 g) and piperidine (0.85 g=0.99 ml) were ground intimately in agate mortar until the starting epoxide disappeared on tlc (3 hours). The product was extracted with ethylacetate and the solvent was removed in vacuo. The product may be purified by formation of hydrochloride in 2N hydrochloric acid and regenerating with 10% sodium bicarbonate solution. It was extracted with ethylacetate, dried over anhydrous sodium sulphate, filtered and the solvent was removed in vacuo.

Yield (isolated): 2.14 gms. viscous liquid $[\alpha]D^{25}$=+1.0 (c 1.0 MeOH) ee; 3.5% (chiral HPLC)

The main advantages of the present invention are:

1. Enantiopure β-aminoalcohols that have a high potential as intermediates for the synthesis of wide range of biologically active compounds and as precursors in asymmetric transformations have been prepared from the easily accessible and inexpensive racemic aryloxyepoxides.

2. The reaction involves for the first time chirally stable racemic epoxides in dynamic kinetic resolution in cyclodextrin inclusion complexes by enantiodifferentiating racemisation for the formation of enantiopure products under solid state conditions. This takes place by supramolecular catalysis as seen in enzyme catalysed reactions.

3. The process of the invention circumvents the limitations of kinetic resolution.

4. The process of the invention is a new approach to asymmetric synthesis by supramolecular catalysis involving dynamic kinetic resolution in cyclodextrin complexes under solid state conditions.

We claim:

1. A process for the solid state synthesis of enantiopure β-aminoalcohols having the formula

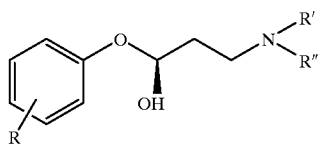

wherein R is alkyl, halo, or alkoxy group, and R' and R" is alkyl or cycloalkyl, from racemic epoxides which comprises:

(a) preparing inclusion complexes of aryloxyepoxide with cyclodextrin by adding an epoxide in equimolar ratio in an organic solvent to an aqueous solution of cyclodextrin at a temperature ranging between 30–80° C.;

(b) reacting the cyclodextrin complex of aryloxyepoxide with a nucleophile in solid state by intimately grinding the mixture using a mortar and pestle;

(c) continuing the mixing till the starting epoxide disappeared on tlc within a period ranging between 3–12 hours;

(d) removing excess amines under vacuum;

(e) extracting the β-aminoalcohols with a solvent with yields of more than 50% and enantioselectivity of up to 100%.

2. A process as claimed in claim 1 wherein the substrates forming the inclusion complexes with cyclodextrins are selected from aryloxy epoxides that are optionally substituted with halo, alkyl or substituted alkyl.

3. A process as claimed in claim 1 wherein the cyclodextrins that form an inclusion complexes with aryloxyepoxides are cyclic oligosaccharides comprising six glucose units (α-cyclodextrin), seven glucose units (β-cyclodextrin) or eight glucose units (γ-cyclodextrin).

4. A process as claimed in claim 1 wherein the epoxide cyclodextrin complexes are prepared by adding the epoxide in equimolar ratio in a solvent to an aqueous solution of cyclodextrin.

5. A process as claimed in claim 1 wherein the reaction of cyclodextrin complex of the aryloxyepoxide with amines is carried out in solid state by intimately grinding the mixture using mortar and pestle or in liquid state using water as a reaction medium.

6. A process as claimed in claim 1 wherein the solvents used for preparing inclusion complexes are selected from the group comprising of methanol, ethanol, and acetone.

7. A process as claimed in claim 1 wherein the solvent used for extracting the aminoalcohols are selected from the group comprising of dichloromethane, chloroform, ethyl acetate and methanol.

8. A process as claimed in claim 1 wherein the nucleophiles used are amines.

9. The process of claim 4, wherein the solvent is methanol, ethanol, acetone, or any combination of any of the foregoing.

* * * * *

UNITED STATES PATENT AND TRADEMARK OFFICE
CERTIFICATE OF CORRECTION

PATENT NO. : 6,239,313 B1
DATED : May 29, 2001
INVENTOR(S) : Rama Rao Kakulapati et al.

It is certified that error appears in the above-identified patent and that said Letters Patent is hereby corrected as shown below:

<u>Title page,</u>
Please add -- [30], Foreign Application Priority Data,

-- INDIA 127/DEL 2000 02/16/00 --.

Signed and Sealed this

Fifteenth Day of January, 2002

Attest:

Attesting Officer

JAMES E. ROGAN
*Director of the United States Patent and Trademark Office*